(12) United States Patent
Puckette

(10) Patent No.: US 7,301,054 B1
(45) Date of Patent: Nov. 27, 2007

(54) PROCESS FOR THE PREPARATION OF GLYCOLALDEHYDE

(75) Inventor: Thomas Allen Puckette, Longview, TX (US)

(73) Assignee: Eastman Chemical Company, Kingsport, TN (US)

(*) Notice: Subject to any disclaimer, the term of this patent is extended or adjusted under 35 U.S.C. 154(b) by 0 days.

(21) Appl. No.: 11/693,542

(22) Filed: Mar. 29, 2007

Related U.S. Application Data

(60) Provisional application No. 60/827,486, filed on Sep. 29, 2006.

(51) Int. Cl.
*C07C 45/50* (2006.01)

(52) U.S. Cl. .................................. 568/454; 568/458

(58) Field of Classification Search .................... None
See application file for complete search history.

(56) References Cited

U.S. PATENT DOCUMENTS

| | | | |
|---|---|---|---|
| 3,560,539 A | 2/1971 | Booth | |
| 3,920,753 A | 11/1975 | Yukawa et al. | |
| 3,948,965 A | 4/1976 | Cawse | |
| 4,072,720 A | 2/1978 | Haag et al. | |
| 4,291,179 A | 9/1981 | Goetz et al. | |
| 4,317,946 A | 3/1982 | Costa | |
| 4,321,414 A | 3/1982 | Costa | |
| 4,362,820 A | 12/1982 | Kaplan | |
| 4,390,734 A | 6/1983 | Knifton | |
| 4,405,814 A | 9/1983 | Carroll et al. | |
| 4,450,299 A | 5/1984 | Oswald et al. | |
| 4,477,685 A | 10/1984 | Chan | |
| 4,503,260 A | 3/1985 | Auvil et al. | |
| 4,533,756 A | 8/1985 | Lin et al. | |
| 4,533,774 A | 8/1985 | Griggs | |
| 4,560,806 A | 12/1985 | Jacobson | |
| 4,590,298 A | 5/1986 | Che | |
| 4,608,444 A | 8/1986 | Jacobson | |
| 4,687,866 A | 8/1987 | Oswald et al. | |
| 4,687,874 A | 8/1987 | Oswald et al. | |
| 4,740,525 A | 4/1988 | Maerkl et al. | |
| 4,847,423 A | 7/1989 | Koprowski et al. | |
| 5,059,710 A | 10/1991 | Abatjoglou et al. | |
| 5,756,855 A | 5/1998 | Abatjoglou et al. | |
| 5,840,647 A | 11/1998 | Puckette et al. | |
| 6,130,358 A | 10/2000 | Tolleson et al. | |
| 6,191,324 B1 | 2/2001 | Guram et al. | |
| 6,515,161 B1 | 2/2003 | Kreutzer et al. | |
| 6,677,268 B2 | 1/2004 | Hillebrand et al. | |
| 6,693,219 B2 | 2/2004 | Puckette et al. | |
| 6,831,035 B2 | 12/2004 | Puckette et al. | |
| 6,846,960 B2 | 1/2005 | Tolleson et al. | |
| 6,906,225 B2 | 6/2005 | Puckette et al. | |
| 6,995,292 B2 | 2/2006 | Tolleson et al. | |
| 2004/0059153 A1 | 3/2004 | Magna et al. | |
| 2004/0152928 A1 | 8/2004 | Drent et al. | |

FOREIGN PATENT DOCUMENTS

| | | |
|---|---|---|
| EP | 0002908 | 7/1979 |
| EP | 0331512 | 9/1989 |
| JP | 57-118527 | 7/1982 |
| JP | 62-209032 | 9/1987 |
| SU | 1310383 | 5/1987 |
| WO | WO 2005-058788 | 6/2005 |
| WO | WO 2005-063668 | 7/2005 |

OTHER PUBLICATIONS

Baricelli et al, "*Homogeneous Catalysis Reaction of Formaldehyde with Synthesis Gas Using Rhodium Complexes*" http://www.scielo.cl/scielo.php?script=sci_arttext&pid=S036616442000000300008& Ing=en&nrm=iso&ting=en (believed to have been downloaded Jul. 14, 2006).

Chan et al, "*Rhodium-Catalyzed Hydroformylation of Formaldehyde*", Journal of Molecular Catalysis, 19, (1983) pp. 377-391.

Jacobson, "Formaldehyde Hydroformylation to Glycol Aldehyde Via Rhodium Phosphine-Amine and Phospine-Amide Catalysts", Journal of Molecular Catalysis, 41 (1987) pp. 163-183.

Marchionna et al, "*Hydroformylation of Formaldehyde Catalyzed by $Rh_4(CO)_{12}$ In the Presence of Phosphine Ligands and Acids (*)*", Gazzetta Chimica Italiana, 116 (1986) pp. 453-457.

Marchionna, M. "Oxygenates by Homologation of CO Hydrogenation With Metal Complexes" in *Catalysis By Metal Complexes*, vol. 16 (1994), Edited by G. Braca; Kluwer Academic Publishers (Dordrecht), pp. 191-219.

Co-pending U.S. Appl. No. 11/670,628, filed on Feb. 2, 2007 (D80524).

*Primary Examiner*—Sikarl A. Witherspoon
(74) *Attorney, Agent, or Firm*—Eric D. Middlemas; Bernard J. Graves, Jr.

(57) ABSTRACT

Disclosed are catalyst solutions for the hydroformylation of formaldehyde comprising one or more fluorophosphite compounds, rhodium and a hydroformylation solvent comprising at least one N,N-disubstituted amide, N-substituted cyclic amide, or a mixture thereof. Also disclosed are hydroformylation processes wherein formaldehyde is contacted with carbon monoxide, hydrogen one or more fluorophosphite compounds, rhodium and a hydroformylation solvent to produce glycolaldehyde. The fluorophosphite-based catalysts provide good reaction rates and high selectivity to glycolaldehyde.

17 Claims, No Drawings

PROCESS FOR THE PREPARATION OF GLYCOLALDEHYDE

CROSS REFERENCES TO RELATED APPLICATIONS

This application claims the benefit of U.S. Provisional Application Ser. No. 60/827,486, filed Sep. 29, 2006, which is incorporated herein by reference in its entirety.

FIELD OF THE INVENTION

This invention pertains to catalyst solutions and processes for the hydroformylation of formaldehyde to glycolaldehyde. More specifically, this invention pertains to catalyst solutions that comprise one or more fluorophosphite ligands, rhodium and a hydroformylation solvent, and processes in which formaldehyde is contacted with carbon monoxide, hydrogen, one or more fluorophosphite compounds, rhodium and a hydroformylation solvent to produce glycolaldehyde.

DETAILED DESCRIPTION

The rhodium-catalyzed hydroformylation of formaldehyde has traditionally been a disfavored process because of the low activity of the rhodium catalyst. The reaction rate can be increased by the addition of promoters such as amines or strong acids; however, the presence of such promoters can lead to the formation of aldol condensation products and other undesirable by-products that can require additional purification steps and expense. If the glycolaldehyde is to be used for the preparation of ethylene glycol, the addition of promoters also can poison the hydrogenation catalysts used in the conversion of glycolaldehyde to ethylene glycol. New catalysts are needed for the hydroformylation of formaldehyde that do not require the presence of promoters to provide high reaction rates. I have now discovered that catalyst solutions that comprise one or more fluorophosphite ligands, rhodium and a hydroformylation solvent provide greatly improved reaction rates for the hydroformylation of formaldehyde to glycolaldehyde without the use of additional promoters. One aspect of the my invention, therefore, is a catalyst solution, comprising:

(i) at least one fluorophosphite compound having the general formula (I):

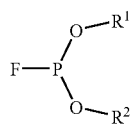

(I)

wherein $R^1$ and $R^2$ are hydrocarbyl radicals which contain a total of up to about 40 carbon atoms;
(ii) rhodium; and
(iii) a hydroformylation solvent comprising at least one N,N-disubstituted amide, N-substituted cyclic amide, or a mixture thereof;

wherein the ratio of gram moles fluorophosphite compound to gram atoms rhodium is about 1:1 to about 100:1.

Another aspect of my invention is a process for the preparation of glycolaldehyde utilizing a catalyst solution comprising a fluorophosphite ligand and rhodium. My invention, therefore, also provides a process for the preparation of glycolaldehyde comprising contacting formaldehyde, hydrogen and carbon monoxide with a catalyst solution, comprising:

(i) at least one fluorophosphite compound having the general formula (I):

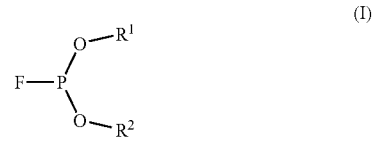

(I)

wherein $R^1$ and $R^2$ are hydrocarbyl radicals which contain a total of up to about 40 carbon atoms;
(ii) rhodium; and
(iii) a hydroformylation solvent;

wherein the ratio of gram moles fluorophosphite compound to gram atoms rhodium is about 1:1 to about 100:1.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the claims, the singular forms "a," "an" and "the" include their plural referents unless the context clearly dictates otherwise. For example, references to a "promoter," or a "reactor" is intended to include the one or more promoters or reactors. References to a composition or process containing or including "an" ingredient or "a" step is intended to include other ingredients or other steps, respectively, in addition to the one named.

The terms "containing" or "including", are synonymous with the term "comprising", and is intended to mean that at least the named compound, element, particle, or method step, etc., is present in the composition, article, or method, but does not exclude the presence of other compounds, catalysts, materials, particles, method steps, etc, even if the other such compounds, material, particles, method steps, etc., have the same function as what is named, unless expressly excluded in the claims.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and the recited lettering can be arranged in any sequence, unless otherwise indicated.

The term "solution", as used herein, is understood to mean that the phosphorus compound and rhodium components are substantially (i.e., 95 or greater weight percent of the phosphorus compound and rhodium) dissolved in the hydroformylation solvent to form a homogeneous mixture. The term "fluorophosphite", as used herein, is understood to mean a trivalent phosphorus compound which is substituted with two oxygen atoms and one fluorine atom. The term "ligand", as used herein, is intended to have its commonly accepted meaning as would be understood by persons having ordinary skill in the art, that is a molecule, atom, ion, or group of atoms bound to a central atom in a chelate or coordination compound. In the present invention, fluorophosphites can serve as ligands bound to a central rhodium atom. The term "hydroformylation", as used herein, also is understood to have its commonly accepted meaning of a catalytic process in which hydrogen and carbon monoxide are reacted with a double bond resulting in the net addition of a formyl group and hydrogen across that double bond. The double bond typically is a carbon-carbon double bond but, as in the case of the present invention, also can be the carbon-oxygen double bound of formaldehyde. The term "formaldehyde", as used herein, is intended to include monomeric formaldehyde and any formaldehyde source that is readily converted to formaldehyde under the conditions of the hydroformylation reaction. For example, "formaldehyde", as used herein, would include formaldehyde in its monomeric form as well as its various acetals, hemiacetals, and low molecular weight oligomers such as, for example, paraformaldehyde. Similarly, the term "glycolaldehyde", is intended to include 2-hydroxy-acetaldehyde and any derivatives thereof such as, for example, acetals, ethers, hemiacetals, oligomers, and hydrogenated products, that may be produced from glycolaldehyde under hydroformylation reaction conditions.

The preparation of glycolaldehyde by the hydroformylation formaldehyde can be carried out by combining formaldehyde with a rhodium catalyst in the presence of a mixture of hydrogen and carbon monoxide. I have found that a specific group of phosphorus acid esters, fluorophosphites, can be used as the phosphorus ligand in the hydroformylation of formaldehyde. Thus, the ligands for the present invention are trivalent phosphorus compounds having the formula (I):

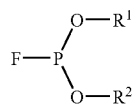

I

The hydrocarbyl groups represented by $R^1$ and $R^2$ may be the same or different, separate or combined, and are selected from unsubstituted and substituted alkyl, cycloalkyl, aralkyl, and aryl groups containing a total of up to about 40 carbon atoms. The total carbon content of substituents $R^1$ and $R^2$ preferably is in the range of about 2 to 35 carbon atoms. Examples of the alkyl groups which $R^1$ and/or $R^2$ separately or individually can represent include ethyl, butyl, pentyl, hexyl, 2-ethylhexyl, octyl, decyl, dodecyl, octadecyl and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. Cyclopentyl, cyclohexyl and cycloheptyl are examples of the cycloalkyl groups $R^1$ and/or $R^2$ individually can represent. The cycloalkyl groups may be substituted with alkyl or any of the substituents described with respect to the possible substituted alkyl groups. Typical examples of alkyl, cycloalkyl, and aralkyl groups which $R^1$ and/or $R^2$ individually can represent are alkyl radicals containing up to about 8 carbon atoms, benzyl, cyclopentyl, cyclohexyl, and cycloheptyl.

Examples of the aryl groups which $R^1$ and/or $R^2$ individually can represent include, but are not limited to, carbocyclic aryl groups such as phenyl, naphthyl, anthracenyl, and substituted derivatives thereof. For example, $R^1$ and/or $R^2$ individually can represent aryl radicals having formulas (II-IV):

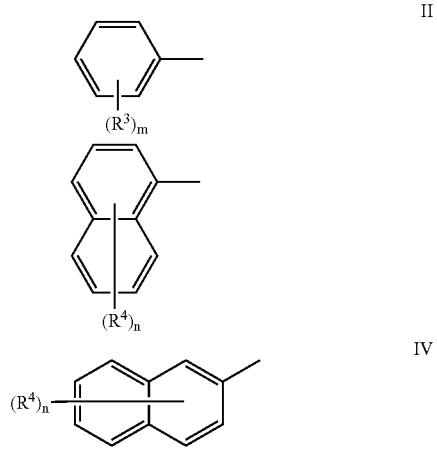

wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contains up to about 8 carbon atoms. Although it is possible for m to represent 0 to 5 and for n to represent 0 to 7, the value of each of m and n usually will not exceed 2. Typically, $R^3$ and $R^4$ represent lower alkyl groups, i.e., straight-chain and branched-chain alkyl of up to about 4 carbon atoms, and m and n each represent 0, 1 or 2.

Alternatively, $R^1$ and $R^2$ in combination or collectively may represent a divalent hydrocarbylene group containing up to about 40 carbon atoms, preferably from about 12 to 35 carbon atoms. Examples of such divalent groups include alkylene of about 2 to 12 carbon atoms, cyclohexylene and arylene. Specific examples of the alkylene and cycloalkylene groups include ethylene, trimethylene, 1,3-butanediyl, 2,2-dimethyl-1,3-propanediyl, 1,1,2-triphenylethanediyl, 2,2,4-trimethyl-1,3-pentanediyl, 1,2-cyclohexylene, and the like. Examples of the arylene groups which $R^1$ and $R^2$ collectively may represent are given hereinbelow as formulas (V), (VI) and (VII).

The divalent groups that $R^1$ and $R^2$ collectively may represent include radicals having the formula

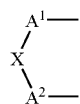

wherein each of $A^1$ and $A^2$ is an arylene radical, e.g., a divalent, carbocyclic aromatic group containing 6 to 10 ring carbon atoms, wherein each ester oxygen atom of fluorophosphite (I) is bonded to a ring carbon atom of $A^1$ and $A^2$.

X is (i) a chemical bond directly between ring carbon atoms of A1 and A2 or (ii) an oxygen atom, a group having the formula —$(CH_2)_y$— wherein y is 2 to 4, or a group having the formula

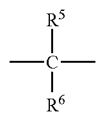

wherein $R^5$ is hydrogen, alkyl or aryl, such as, for example, the aryl groups illustrated by formulas (II), (III) and (IV), and $R^6$ is hydrogen or alkyl. The total carbon content of the group —$C(R^5)(R^6)$— normally will not exceed 20 and, can be in the range of 1 to 8 carbon atoms. Normally, when $R^1$ and $R^2$ collectively represent a divalent hydrocarbylene group, the phosphite ester oxygen atoms, i.e. the oxygen atoms depicted in formula (I), are separated by a chain of atoms containing at least 3 carbon atoms.

Examples of the arylene groups represented by each of $A^1$ and $A^2$ include the divalent radicals having the formulas (V-VII):

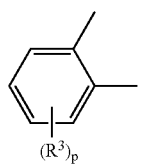

V

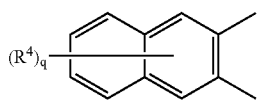

VI

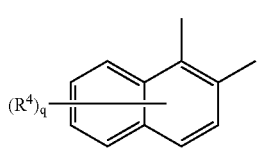

VII wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of such alkyl, alkoxy, alkanoyl, alkoxycarbonyl and alkanoyloxy groups typically contains up to about 8 carbon atoms. Although it is possible for p to represent 0 to 4 and for q to represent 0 to 6, the value of each of p and q usually will not exceed 2. $R^3$ and $R^4$ preferably represent lower alkyl groups, i.e., straight-chain and branched-chain alkyl of up to about 4 carbon atoms, and p and q each represent 0, 1 or 2.

In one embodiment, the fluorophosphite esters can be compounds wherein the fluorophosphite ester oxygen atoms are bonded directly to a ring carbon atom of a carbocyclic, aromatic group, e.g., an aryl or arylene group represented by any of formulas (II) through (VII). When $R^1$ and $R^2$ individually each represents an aryl radical, e.g., a phenyl group, one or both of the ring carbon atoms that are in a position ortho to the ring carbon atoms bonded to the fluorophosphite ester oxygen atom can be substituted with an alkyl group, especially a branched chain alkyl group such as isopropyl, tert-butyl, tert-octyl and the like. Similarly, when $R^1$ and $R^2$ collectively represent a radical having the formula,

the ring carbon atoms of arylene radicals $A^1$ and $A^2$ that are in a position ortho to the ring carbon atoms bonded to the fluorophosphite ester oxygen atom can be substituted with an alkyl group, typically a branched chain alkyl group such as, for example, isopropyl, tert-butyl, tert-octyl and the like. For example, the fluorophosphite esters may have the general formula (VIII):

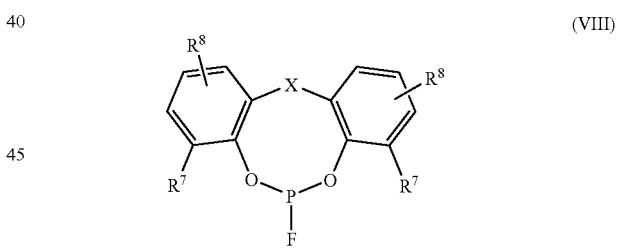

(VIII)

wherein each $R^7$ is halogen or alkyl of 3 to 8 carbon atoms; each $R^8$ is hydrogen, halogen, alkyl of 1 to 8 carbon atoms, or alkoxy of 1 to 8 carbon atoms; and X is (i) a chemical bond directly between ring carbon atoms of each phenylene group to which X is bonded; or (ii) a group having the formula

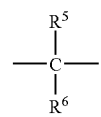

wherein each of $R^5$ and $R^6$ is hydrogen or alkyl of 1 to 8 carbon atoms. In one embodiment, for example, the fluorophosphite can have the following formula (IX):

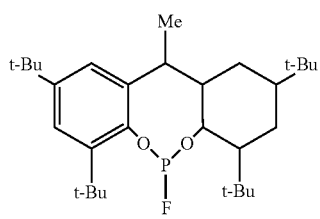

(IX)

wherein t-Bu is tertiary butyl and Me is methyl. Fluorophosphite (IX) is available commercially from Albemarle Corporation under the trademark ETHANOX 398™ (CAS #118337-09-0).

The fluorophosphite compounds of formula (I) may be prepared by published procedures or by techniques analogous thereto, See, for example, the procedures described by Riesel et al., J. Z. Anorg. Allg. Chem., 603, 145 (1991), Tullock et al., J. Org. Chem., 25, 2016 (1960), White et al., J. Am. Chem. Soc., 92, 7125 (1970) and Meyer et al., Z. Naturforsch, Bi. Chem. Sci., 48, 659 (1993) and in U.S. Pat. No. 4,912,155. In addition, some fluorophosphite esters of formula (I) are available commercially such as, for example, fluorophosphite (IX) discussed above.

Rhodium compounds that may be used as a source of rhodium for the active catalyst include rhodium(II) or rhodium(III) salts of carboxylic acids, examples of which include di-rhodium tetraacetate dihydrate, rhodium(II) acetate, rhodium(II) isobutyrate, rhodium(II) 2-ethylhexanoate, rhodium (II) benzoate and rhodium(II) octanoate. Also, rhodium carbonyl species such as $Rh_4(CO)_{12}$, $Rh_6(CO)_{16}$ and rhodium(1) acetylacetonate dicarbonyl may be suitable rhodium feeds. Additionally, in cases where the phosphine moieties of the complex are easily displaced by the fluorophosphite ligands of the present invention, the rhodium component may be introduced into the process as rhodium organophosphine complexes such as, for example, tris(triphenyl-phosphine) rhodium carbonyl hydride. Less desirable rhodium sources are rhodium salts of strong mineral acids such as chlorides, bromides, nitrates, sulfates, phosphates and the like.

The ratio of gram moles fluorophosphite compound to gram atoms rhodium in the hydroformylation catalyst solution and hydroformylation process described herein can vary over a wide range. For example, the gram mole fluorophosphite:gram atom rhodium ratios may be from about 1:1 to about 100:1. Other examples of gram mole fluorophosphite:gram atom rhodium ratios are about 1:1 to about 70:1 and about 1:1 to about 50:1.

The concentration of the rhodium and ligand in the hydroformylation solvent or reaction mixture is not critical for the successful operation of our invention. As mentioned hereinabove, a gram mole ligand:gram atom rhodium ratio of at least 1:1 normally is maintained in the reaction mixture. The absolute concentration of rhodium in the reaction mixture or solution may vary from about 1 mg/liter to about 5000 mg/liter or more. When the process is operated within the practical conditions of this invention, the concentration of rhodium in the reaction solution normally is in the range of about 20 to about 300 mg/liter. Concentrations of rhodium lower than this range generally do not yield acceptable reaction rates and/or require reactor operating temperatures that are so high as to be detrimental to catalyst stability. Higher rhodium concentrations are not generally used because of the high cost of rhodium.

The hydroformylation solvent for the catalyst solution of the invention can comprise amides. Amide solvents generally favor the production of glycolaldehyde over that of methanol and amides which have no free hydrogen on the amido nitrogen atom have been found to favor production of glycol aldehyde over that of methanol. Thus, in one embodiment of my invention, the hydroformylation solvent comprises least one N,N-disubstituted amide or N-substituted cyclic amide. The term "N,N-disubstituted amide", is understood to mean that the amide nitrogen is attached to two organo substituents. For example, the hydroformylation solvent can comprise at least one N,N-disubstituted amide having the formula (X)

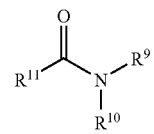

X wherein $R^9$ and $R^{10}$ are independently selected from alkyl radicals containing 1 to 20 carbon atoms, cycloalkyl radicals containing 5 to 20 carbon atoms, aralkyl radicals containing 7 to 12 carbon atoms, and aryl radicals containing 6 to 12 carbon atoms; and $R^{11}$ is independently selected from hydrogen, alkyl radicals containing 1 to 20 carbon atoms, cycloalkyl radicals containing 5 to 20 carbon atoms, aralkyl radicals containing 7 to 12 carbon atoms, and aryl radicals containing 6 to 12 carbon atoms. The alkyl, cycloalkyl, aralkyl, and aryl radicals may be substituted one or more or a mixture of alkyl, alkoxy, cycloalkyl, halogen, or the like, and aralkyl radicals containing 7 to 12 carbon atoms. The amide can be the amide of lower carboxylic acid such as, for example, formic, acetic, propionic, hexanoic, etc, and the substituents on the nitrogen can be alkyl groups, such as, for example lower alkyl groups. For example, in one embodiment, $R^9$ and $R^{10}$ can be independently selected from methyl, ethyl, propyl, butyl, pentyl, isopentyl, hexyl, and heptyl and $R^{11}$ is independently selected from hydrogen, methyl, ethyl, propyl, pentyl, and hexyl. There is some variation in selectivity to glycol aldehyde with the variation in the chain length of the acid amide and the substituents on the nitrogen. The acetamides give particularly good results. A mixture of amides can be used.

Some specific examples of N,N-disubstituted amides that may be used as the hydroformylation solvent include N,N-dimethylformamide, N,N-dimethylacetamide, N,N-diethylformamide, N,N-diethylacetamide, N,N-diethyldodecanamide, N,N-dibutyldodecanamide, N-methyl-N-butyldodecanamide, N,N-diethyltetradecanamide, N,N-dicyclohexyldecanamide, N,N-dibutylbenzamide, N,N-dibenzyloctanamide, and combinations of one or more of these compounds. The hydroformylation solvent also may comprise a cyclic amide such as, for example, N-methyl-2-pyrrolidinone. These compounds are either commercially available or can be prepared by known reactions. It is understood that any of the above amides may be used in combination with any of the fluorophosphite compounds described above in any combination and in any ratio with rhodium described herein. For example, the above N,N-disubstituted amides described above and/or N-methyl-2-pyrrolidinone may be used in any combination with the fluorophosphite compounds represented by formulas (VII) or (IX).

My invention also provides a process for preparing glycolaldehyde which comprises contacting formaldehyde, hydrogen and carbon monoxide with a catalyst solution comprising rhodium and a fluorophosphite compound of formula (I) wherein the ratio of gram moles ligand:gram atom rhodium is about 1:1 to about 100:1.

As described previously, the formaldehyde employed in the process can be utilized in any various forms, including, but not limited to, gaseous formaldehyde, aqueous formaldehyde solutions such as, for example, commercially available formalin containing approximately 40% formaldehyde, trioxane or paraformaldehyde, methylene dicarboxylates, and linear polymers of formaldehyde (i.e., poly(oxymethylene) glycols and derivatives thereof) formed from the polymerization or oligomerization of formaldehyde in water, alcohols, or other solvents. Thus, the term "formaldehyde", as used herein in the context of the current specification and claims, is intended to include all the various forms of formaldehyde described above. In one embodiment, for example, the process may employ paraformaldehyde as the formaldehyde source.

The presence of water in the catalyst solution can reduce the rate of the hydroformylation reaction such that it may be desirable to limit the concentration of water in the catalyst solution. For example, the use of commercial formalin, which contains approximately 60 weight percent water, as a formaldehyde source can severely reduce the rate of the reaction if the concentration of water in the catalyst solution is allowed to become too high. Thus, if water is present in the formaldehyde source, it may be desirable to reduce the overall concentration of water introduced into the reaction by using a feedstock having high concentration of formaldehyde or mixing the aqueous formaldehyde source with a non-aqueous source such as, for example, paraformaldehyde. In one embodiment of the process of the invention, for example, the catalyst solution can have a water concentration of 10 weight percent or less, based on the total weight of the catalyst solution. Other examples of water concentrations in the catalyst solution are 8 weight percent or less, 6 weight percent or less, 4 weight percent or less, 2 weight percent or less, and 0.5 weight percent or less.

The fluorophosphite compounds may any of the compounds having the general formula (I) as described hereinabove and in any combination. For example, as described previously, $R^1$ and $R^2$ individually can be independently selected from alkyl radicals of up to 8 carbon atoms, benzyl, cyclopentyl, cyclohexyl, cycloheptyl, and aryl groups having formulas (II-IV):

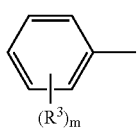

II

-continued

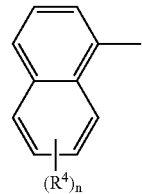

III

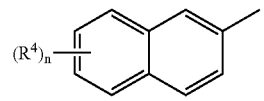

IV wherein $R^3$ and $R^4$ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to 8 carbon atoms; m and n each is 0, 1 or 2; and the total carbon atom content of the hydrocarbyl radicals represented by $R^1$ and $R^2$ is 2 to 35. In another example, $R^1$ and $R^2$ collectively represent alkylene of 2 to 12 carbon atoms, cyclohexylene, an arylene group having the formulas (V-VII):

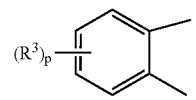

(V)

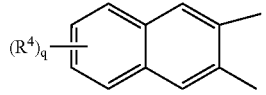

(VI)

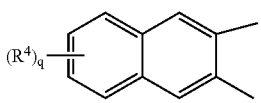

(VII)

or a radical having the formula

wherein
each of $A^1$ and $A^2$ is an arylene radical having formula (V), (VI) or (VII) above wherein each ester oxygen atom of fluorophosphite (I) is bonded to a ring carbon atom of $A^1$ and $A^2$;

X is (i) a chemical bond directly between ring carbon atoms of $A^1$ and $A^2$; or (ii) an oxygen atom, a group having the formula $-(CH_2)_y-$ wherein y is 2 to 4, or a group having the formula

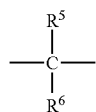

wherein $R^5$ is hydrogen, alkyl or aryl; $R^6$ is hydrogen or alkyl; and the group —C($R^5$)($R^6$)— contains up to 8 carbon atoms; and wherein $R^3$ and $R^4$ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to about 8 carbon atoms; and p and q each is 0, 1 or 2. In yet another example, the fluorophosphite compound has formula (VIII):

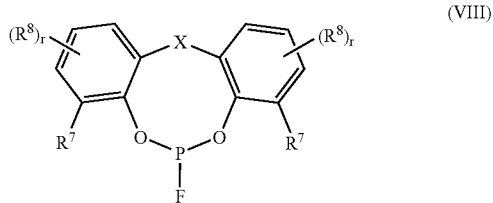

(VIII)

wherein $R^7$ represents halogen or $C_3$ to $C_8$ alkyl; $R^8$ represents hydrogen, halogen, $C_1$ to $C_8$ alkyl, or $C_1$ to $C_8$ alkoxy; r is 0, 1 or 2; and X is a group having the formula

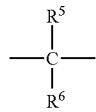

wherein $R^5$ and $R^6$ each are hydrogen or alkyl. In still another example, the fluorophosphite compound has formula (IX):

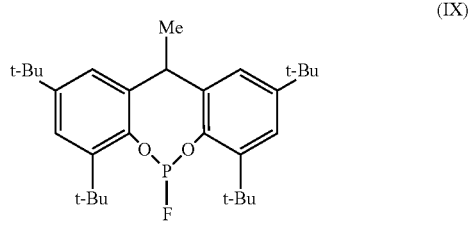

(IX)

wherein t-Bu is tertiary butyl and Me is methyl.

The ratio of gram moles fluorophosphite compound to gram atoms rhodium in the hydroformylation process are as described previously. For example, the gram mole fluorophosphite:gram atom rhodium ratios may be from about 1:1 to about 100:1. Other examples of gram mole fluorophosphite:gram atom rhodium ratios are about 1:1 to about 70:1 and about 1:1 to about 50:1.

The concentration of the rhodium and fluorophosphite ligand in the hydroformylation solvent or reaction mixture is not critical for the successful operation of our invention. As mentioned hereinabove, a gram mole ligand:gram atom rhodium ratio of at least 1:1 normally is maintained in the reaction mixture. The absolute concentration of rhodium in the reaction mixture or solution may vary from about 1 mg/liter to about 5000 mg/liter or more. When the process is operated within the practical conditions of this invention, the concentration of rhodium in the reaction solution normally is in the range of about 20 to about 300 mg/liter.

The hydroformylation solvent for the process of the invention can be selected from alkanes, cycloalkanes, alkenes, amides, cycloalkenes, carbocyclic aromatic compounds, esters, ketones, acetals, ethers, and mixtures thereof. As described previously, amides which have no free hydrogen on the amido nitrogen atom have been found to favor production of glycol aldehyde over that of methanol. Thus, in one embodiment of my hydroformylation process, the hydroformylation solvent comprises least one N,N-disubstituted amide, at least one N-substituted cyclic amide, or a mixture thereof. Examples of N,N-disubstituted amides include those amides having the formula (X)

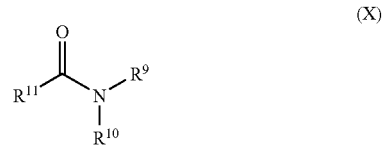

(X)

wherein $R^9$ and $R^{10}$ are independently selected from alkyl radicals containing 1 to 20 carbon atoms, cycloalkyl radicals containing 5 to 20 carbon atoms, aralkyl radicals containing 7 to 12 carbon atoms, and aryl radicals containing 6 to 12 carbon atoms; and $R^{11}$ is independently selected from hydrogen, alkyl radicals containing 1 to 20 carbon atoms, cycloalkyl radicals containing 5 to 20 carbon atoms, aralkyl radicals containing 7 to 12 carbon atoms, and aryl radicals containing 6 to 12 carbon atoms. The alkyl, cycloalkyl, aralkyl, and aryl radicals may be substituted one or more or a mixture of alkyl, alkoxy, cycloalkyl, halogen, or the like, and aralkyl radicals containing 7 to 12 carbon atoms. For example, $R^9$ and $R^{10}$ can be independently selected from methyl, ethyl, propyl, butyl, pentyl, isopentyl, hexyl, and heptyl and $R^{11}$ is independently selected from hydrogen, methyl, ethyl, propyl, pentyl, and hexyl.

Some specific examples of N,N-disubstituted amides that may be used as the hydroformylation solvent include N,N-dimethylformamide, N,N-dimethylacetamide, N,N-diethylformamide, N,N-diethylacetamide, N,N-diethyldodecanamide, N,N-dibutyldodecanamide, N-methyl-N-butyldodecanamide, N,N-diethyltetradecanamide, N,N-dicyclohexyldecanamide, N,N-dibutylbenzamide, N,N-dibenzyloctanamide, and combinations of one or more of these compounds. The hydroformylation solvent also may comprise a cyclic amide such as, for example, N-methyl-2-pyrrolidinone. These compounds are either commercially available or can be prepared by known reactions. It is understood that any of the above amides may be used in combination with any of the fluorophosphite compounds described above in any combination and in any ratio with the rhodium as described herein. For example, the above N,N-disubstituted amides described above and/or N-methyl-2-pyrrolidinone may be used in any combination with the fluorophosphite compounds represented by formulas (VIII) or (IX).

The catalyst solution may comprise other catalyst metals, ligands, solvents, and promoters in addition to the fluorophosphite compounds, rhodium, and hydroformylation solvents described above. For example, Lewis and Bronsted acids such as, for example, ZnCl$_2$ and p-toluenesulfonic acid, can be added to the catalyst solution to enhance the rate or selectivity of the hydroformylation reaction. Other examples of promoters include amine bases such as triethyl amine. These promoters, however, also can have detrimental effects on the catalyst and selectivity of the reaction. For example, the presence of strong acids, such as p-toluenesulfonic acid, can cause the eventual decomposition of the fluorophosphite compound. Similarly, amines can catalyze the aldol condensation of the product glycolaldehyde with itself to form heavy byproducts.

The reaction conditions used are not critical for the operation of the process and conventional hydroformylation conditions normally are used. The process may be carried out at temperatures in the range of about 20° to 200° C., the preferred hydroformylation reaction temperatures are from 50° to 135° C. with the most favored reaction temperatures ranging from 75° to 125° C. Higher reactor temperatures are not favored because of increased rates of catalyst decomposition while lower reactor temperatures result in relatively slow reaction rates. The total reaction pressure may range from about 1 bar to about 350 bars absolute (about 5000 psig). As another example, the pressure can range from about 105 to about 175 bars absolute (about 1 500 to 2500 psig).

The hydrogen:carbon monoxide mole ratio in the reactor likewise may vary considerably ranging from 10:1 to 1:10 and the sum of the absolute partial pressures of hydrogen and carbon monoxide may range from 0.5 to 350 bars absolute. The ratios of the hydrogen to carbon monoxide in the synthesis gas (synthesis gas or "syngas" is a mixture of gases comprising various ratios of carbon monoxide and hydrogen) can be readily changed by the addition of either hydrogen or carbon monoxide to the syngas stream.

Another embodiment of the invention is a process for the preparation of glycolaldehyde consisting essentially of contacting formaldehyde, hydrogen and carbon monoxide with a catalyst solution, consisting essentially of:

(i) at least one fluorophosphite compound having the general formula (I):

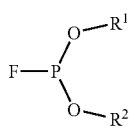
I wherein R$^1$ and R$^2$ collectively represent alkylene of 2 to 12 carbon atoms, cyclohexylene, an arylene group having the formula

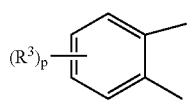
(V)

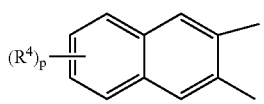
(VI)

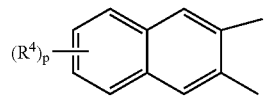
(VII)

or a radical having the formula

wherein
each of A$^1$ and A$^2$ is an arylene radical having formula (V), (VI) or (VII) above wherein each ester oxygen atom of fluorophosphite (I) is bonded to a ring carbon atom of A$^1$ and A$^2$;
X is (i) a chemical bond directly between ring carbon atoms of A$^1$ and A$^2$; or (ii) an oxygen atom, a group having the formula —(CH$_2$)$_y$— wherein y is 2 to 4, or a group having the formula

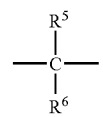

wherein
R$^5$ is hydrogen, alkyl or aryl; R$^6$ is hydrogen or alkyl; and the group —C(R$^5$)(R$^6$)— contains up to 8 carbon atoms; and wherein
R$^3$ and R$^4$ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to about 8 carbon atoms; and p and q each is 0, 1 or 2;
(ii) rhodium; and
(iii) a hydroformylation solvent consistently essentially of at least one N,N-disubstituted amide, N-substituted cyclic amide, or a mixture thereof.

The phrase "consisting essentially of", as used herein, is intended to encompass a process for the preparation of glycolaldehyde by contacting formaldehyde, hydrogen and carbon monoxide with a catalyst solution that comprises primarily at least one fluorophosphite ligand in accordance with formula (I) above, rhodium, and a hydroformylation solvent comprising at least one N,N-disubstituted amide, N-substituted cyclic amide, or a mixture thereof. It is understood to exclude any elements that would substantially alter the essential properties of the hydroformylation process to which the phrase refers. Although the process of the present invention is based predominantly on the hydroformylation solution as described above, it is within the scope of the invention that the catalyst solution also may contain other catalysts, solvents, promoters, and ligands, as long as the hydroformylation reaction rate is not significantly reduced in comparison to the rate of a catalyst solution, under identical reaction condition, in which the additional catalysts, solvents, promoters, and ligands are absent. By "significantly reduced", it is meant that the reaction rate is reduced by 70% or more. For example, the addition of formaldehyde source containing a high level of water at a concentration that would lead to a reduction in rate by 70% or more would be excluded from this embodiment of the invention. By contrast, the addition of a promoter that increases the rate of the reaction would not be excluded from the scope of the claims.

The above process is understood to include the various embodiments of the fluorophosphite compound, rhodium, amide hydroformylation solvent, formaldehyde source, and process conditions described hereinabove. For example, the fluorophosphite compound can have formula (VIII):

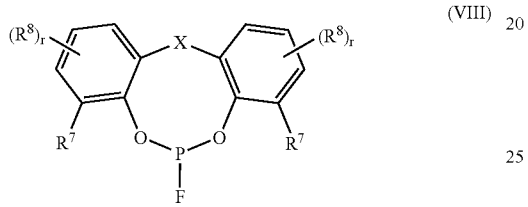

wherein $R^7$ represents halogen or $C_3$ to $C_8$ alkyl; $R^8$ represents hydrogen, halogen, $C_1$ to $C_8$ alkyl, or $C_1$ to $C_8$ alkoxy; r is 0, 1 or 2; and X is a group having the formula

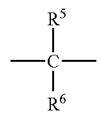

wherein $R^5$ and $R^6$ each are hydrogen or alkyl. In another example, the fluorophosphite compound has formula (IX):

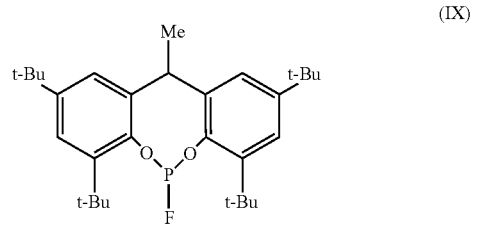

wherein t-Bu is tertiary butyl and Me is methyl.

The hydroformylation solvent consists essentially of at least one N,N-disubstituted amide, N-substituted cyclic amide, or combination thereof. Some specific examples of solvents include N-methyl-2-pyrrolidinone; N,N-dimethylformamide; N,N-diethylformamide; N,N-diethylacetamide; N,N-diethyldodecanamide; N,N-dibutyldodecanamide; N-methyl-N-butyl-dodecanamide; N,N-diethyltetradecanamide; N,N-dicyclohexyldecanamide, N,N-dibutylbenzamide; and N,N-dibenzyloctanamide. Other solvents may be present, provided the additional solvents do not significantly reduce the rate of the hydroformylation reaction as described above.

Any of the known hydroformylation reactor designs or configurations may be used in carrying out the process provided by the present invention. For example, the process also may be practiced in a batchwise manner by contacting the olefin, hydrogen and carbon monoxide with the present catalyst in an autoclave. In another example, a reactor design where catalyst and feedstock are pumped into a reactor and allowed to overflow with product glycolaldehyde, i.e. liquid overflow reactor design, is also suitable. For example, glycolaldehyde product may be prepared in a continuous manner with the glycolaldehyde product being removed from the reactor zone as a liquid in combination with the catalyst. The glycolaldehyde product may be separated from the catalyst by conventional means such as by distillation or extraction and the catalyst then recycled back to the reactor. A trickle-bed reactor design also is suitable for this process. It will be apparent to those skilled in the art that other reactor schemes may be used with this invention. The various embodiments of the present invention are further illustrated by the following examples.

EXAMPLES

Comparative Example 1

Carbonylation of Formaldehyde with Rhodium and Triphenylphosphine

A 300 ml Autoclave Engineer® autoclave was charged with 0.25 Mole of paraformaldehyde, 50 ml of dimethylacetamide, 1.57 grams of triphenylphosphine and 0.075 grams of rhodium (1) dicarbonyl acetonylacetonate. The reactor was purged with $N_2$ and charged with a 1:1 molar mixture of hydrogen and carbon monoxide to a total pressure of 2000 psig. The reactor was stirred and heated to a temperature of 100° C. for a total time of 2 hours. The reactor was cooled and the excess pressure vented. The contents of the autoclave were examined by gas chromatography using an internal standard method. The analysis of the reactor contents showed 32% conversion of the formaldehyde to products. The selectivity to products was 98.0% to glycol aldehyde and 1.2% to methanol. An additional 0.8% of other products were formed.

Example 1

Hydroformylation catalyst with 2,2'-Ethylidenebis(4,6-di-tert-butylphenyl) fluorophosphite (Ethanox 398™)

The procedure of the comparative example was repeated except that 2.91 grams of 2,2'-ethylidenebis(4,6-di-tert-butylphenyl) fluorophosphite was used as the phosphorus ligand. The ratio of moles fluorophosphite ligand to gram atoms rhodium was approximately 20:1. Analysis of the reaction product showed a 78.3% conversion of formaldehyde to products. The selectivity to products was 99.2% to glycolaldehyde, 0.5% to methanol and 0.3% to unidentified products.

Example 2

Hydroformylation catalyst with 2,2'-methylidenebis (4-tert-butyl-6-methylphenyl) fluorophosphite The procedure of the comparative example was repeated except that 1.36 grams of 2,2'-methylidenebis(4-tert-butyl- 6-methylphenyl) fluorophosphite was used as the phosphorus ligand. The ratio of moles fluorophosphite ligand to gram atoms rhodium was approximately 12:1. Analysis of the reaction product showed a 35% conversion of formaldehyde to products. The selectivity to products was 95.1% to glycolaldehyde, 1.6% to methanol and 3.3% to unidentified products.

Example 3

Hydroformylation catalyst with O,O'-(2,2'-(3,3,5,5'-tetra-tert-butylbiphenylyl)) phosphorofluoridite The procedure of the comparative example was repeated except that 1.83 grams of O, O'-(2,2'-(3,3',5,5'-tetra-tert-butylbiphenylyl)) phosphorofluoridite was used as the phosphorus ligand. The ratio of moles fluorophosphite ligand to gram atoms rhodium was approximately 13.7:1. Analysis of the recovered reaction material showed a 49% conversion of formaldehyde to products. The selectivity to products was 95.8% to glycolaldehyde, 1.8% to methanol and 2.4% to unidentified products.

Examples 4-27

A series of hydroformylation reactions were carried out under varying conditions of solvent, ligand concentration, promoter, and formaldehyde source. In all experiments, varying amounts of 2,2'-ethylidenebis(4,6-di-tert-butylphenyl) fluorophosphite (ETHANOX™398, available as from Albemarle Corp.) were used as the ligand in the presence of 30 mg of rhodium as the catalyst. The reactions were carried out in a 300 ml Autoclave Engineer® autoclave which was charged with 0.25 mol of either 40% formalin or paraformaldehyde, solvent, and promoter as listed in Table 1. The solvents and promoters listed in Table 1 are abbreviated as follows:

DMAC N,N-dimethylacetamide
DMP N,N-dimethylpropionamide
DMI N,N-dimethylisobutyramide
DMO N,N-dimethyloctylamide
DMN N,N-dimethyl-n-butyramide
DIN N,N-diisopropyl-n-butyramide
DHN N,N-di-n-hexyl-n-butyramide
DHI N,N-di-n-hexylisobutyramide
DMH N,N-dimethyl-n-hexamide
DML N,N-dimethyllaurylamide
$Et_3N$ Triethyl amine
TsOH p-Toluenesulfonic acid
Xyl Xylene
Para Paraformaldehyde The reactor was purged with $N_2$ and charged with a 1:1 molar mixture of hydrogen and carbon monoxide to a total pressure of 2000 psig. The reactor was stirred and heated to a temperature of 100° C. for a total time of 1-3 hours. The reactor was then cooled and the excess pressure vented. The contents of the autoclave were examined by gas chromatography using an internal standard method, and the results are presented in Table 1. No glycolaldehyde product was detected when 40% formalin was used as the source of formaldehyde (Examples 13 and 18). In addition, decomposition of the fluorophosphite ligand was observed when p-toluenesulfonic acid was present as a promoter. The presence of triethyl amine resulted in the formation of heavy by-products, presumably from the aldol condensation of the glycolaldehyde product with itself.

TABLE 1

| Ex. | Ligand (g) | Solvent (amount) | Promoter (g) | $H_2CO$ source | % Conv | % Selectivity to GA | Time (h) |
|---|---|---|---|---|---|---|---|
| 4 | 1.46 | DMAC (50 mL) | $Et_3N$ (0.011) | para | 13.9 | 100 | 1 |
| 5 | 1.46 | DMAC (50 mL) | $Et_3N$ (0.022) | para | 40.9 | 63.7 | 1 |
| 6 | 1.46 | DMAC (50 mL) | $Et_3N$ (0.033) | para | 76 | 8.7 | 1 |
| 7 | 0.48 | DMAC (50 mL) | none | para | 51.3 | 84.4 | 3 |
| 8 | 1.46 | DMAC (50 mL) | none | para | 42.1 | 89.9 | 3 |
| 9 | 2.92 | DMP (50 mL) | none | para | 6.4 | 98.7 | 1 |
| 10 | 2.92 | DMI (50 mL) | none | para | 15.1 | 66.3 | 1 |
| 11 | 2.92 | DMO (50 mL) | none | para | 10.8 | 83.0 | 1 |
| 12 | 2.92 | DIN (50 mL) | none | formalin | 0 | n/a | 1 |
| 13 | 2.91 | DMAC (40 mL) Xyl (10 mL) | none | para | 21.7 | 96.6 | 2 |
| 14 | 3.89 | DHN (40 g) Xyl (10 mL) | none | para | 2.4 | 99.0 | 1 |
| 15 | 3.89 | DHI (40 g) Xyl (10 mL) | none | para | 3.0 | 99.0 | 1 |
| 16 | 2.92 | DIN (40 g) Xyl (10 mL) | none | para | 7.6 | 86.4 | 1 |
| 17 | 2.92 | DIN (20 g) Xyl (30 mL) | none | formalin | 0 | n/a | 1 |
| 18 | 1.46 | DMAC (50 mL) | TsOH (0.10) | para | 54.7 | 92.2 | 1 |
| 19 | 1.46 | DMAC (50 mL) | TsOH (0.20) | para | 81.4 | 81.7 | 1 |
| 20 | 1.46 | DMAC (50 mL) | TsOH (0.40) | para | 84.4 | 90.8 | 3 |
| 21 | 1.46 | DML (50 mL) | TsOH (0.40) | para | 16.2 | 90.1 | 1 |
| 22 | 1.46 | DMH (50 mL) | TsOH (0.40) | para | 24.7 | 68.4 | 1 |
| 23 | 1.46 | DMP (50 mL) | TsOH (0.40) | para | 48.3 | 91.6 | 1 |
| 24 | 2.92 | DMP (50 mL) | TsOH (0.40) | para | 40.6 | 68.5 | 1 |
| 25 | 4.30 | DMH (50 mL) | TsOH (0.40) | para | 36.2 | 73.0 | 1 |
| 26 | 2.92 | DMO (50 mL) | TsOH (0.40) | para | 39.2 | 84.4 | 1 |
| 27 | 2.92 | DMAC (50 mL) | $ZnCl_2$ (0.32) | para | 34.3 | 91.3 | 1 |

I claim:

1. A process for the preparation of glycolaldehyde comprising contacting formaldehyde, hydrogen and carbon monoxide with a catalyst solution, comprising:
   (i) at least one fluorophosphite compound having the general formula (I):

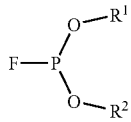

wherein R¹ and R² are hydrocarbyl radicals which contain a total of up to 40 carbon atoms;

(ii) rhodium; and (iii) a hydroformylation solvent;

wherein the ratio of gram moles fluorophosphite compound to gram atoms rhodium is from about 1:1 to about 100:1.

2. The process according to claim 1 wherein the concentration of rhodium in the solution is about 20 to about 300 mg per liter and the process is carried out at a temperature of about 50 to about 135° C. at a pressure of about 1 bar to about 350 bars absolute.

3. The process according to claim 2 wherein $R_1$ and $R^2$ individually are independently selected from alkyl radicals of up to 8 carbon atoms, benzyl, cyclopentyl, cyclohexyl, cycloheptyl, and aryl groups having formulas (II-IV):

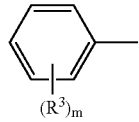

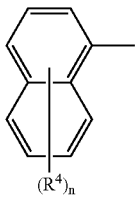

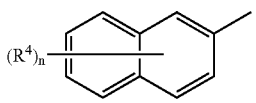

wherein R³ and R⁴ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to 8 carbon atoms; m and n each is 0, 1 or 2; and the total carbon atom content of the hydrocarbyl radicals represented by R¹ and R² is 2 to 35 and wherein the ratio of gram moles fluorophosphite compound to gram atoms rhodium is about 1:1 to about 70:1.

4. The process according to claim 3 wherein said formaldehyde comprises paraformaldehyde.

5. The process according to claim 2 wherein R¹ and R² collectively represent a divalent hydrocarbylene group containing about 12 to 35 carbon atoms.

6. The process according to claim 5 wherein the ratio of gram moles fluorophosphite compound to gram atoms rhodium is about 1:1 to about 70:1 and R¹ and R² collectively represent alkylene of 2 to 12 carbon atoms, cyclohexylene, an arylene group having the formula

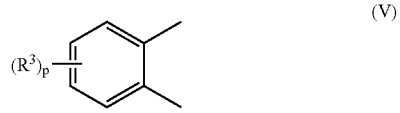

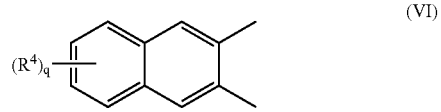

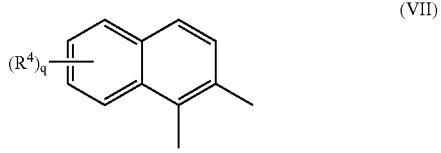

or a radical having the formula

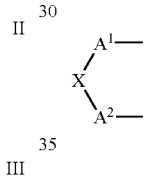

wherein each of A¹ and A² is an arylene radical having formula (V), (VI) or (VII) above wherein each ester oxygen atom of fluorophosphite (I) is bonded to a ring carbon atom of A¹ and A²;

X is (i) a chemical bond directly between ring carbon atoms of A¹ and A²; or (ii) an oxygen atom, a group having the formula —(CH₂)ᵧ— wherein y is 2 to 4, or a group having the formula

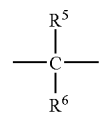

wherein

R⁵ is hydrogen, alkyl or aryl; R⁶ is hydrogen or alkyl; and the group —C(R⁵)(R⁶)— contains up to 8 carbon atoms; and wherein R³ and R⁴ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to about 8 carbon atoms; and p and q each is 0, 1 or 2.

7. The process according to claim 6 wherein said fluorophosphite compound has formula (VIII):

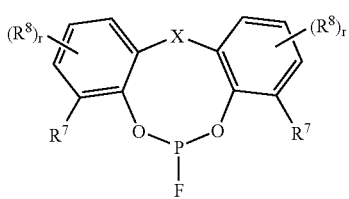

wherein $R^7$ represents halogen or $C_3$ to $C_8$ alkyl; $R^8$ represents hydrogen, halogen, $C_1$ to $C_8$ alkyl, or $C_1$ to $C_8$ alkoxy; r is 0, 1 or 2; and X is a group having the formula

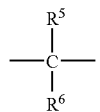

wherein $R^5$ and $R^6$ each are hydrogen or alkyl.

8. The process according to claim 7 wherein said fluorophosphite compound has formula (IX):

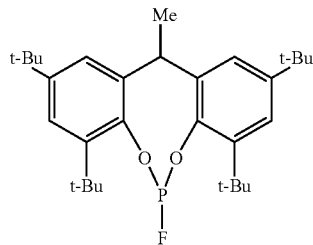

wherein t-Bu is tertiary butyl and Me is methyl.

9. The process according to claim 1 wherein the ratio of gram moles fluorophosphite compound to gram atoms rhodium is about 1:1 to about 50:1 and said hydroformylation solvent is selected from alkanes, cyclo-alkanes, alkenes, amides, cycloalkenes, carbocyclic aromatic compounds, esters, ketones, acetals, ethers, and mixtures thereof.

10. The process according to claim 9 wherein said hydroformylation solvent comprises at least one N-substituted cyclic amide, at least one N,N-disubstituted amide having the following formula (X):

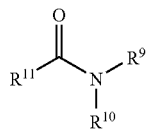

wherein $R^9$ and $R^{10}$ are independently selected from alkyl radicals containing 1 to 20 carbon atoms, cycloalkyl radicals containing 5 to 20 carbon atoms, aralkyl radicals containing 7 to 12 carbon atoms, and aryl radicals containing 6 to 12 carbon atoms; and $R^{11}$ is independently selected from hydrogen, alkyl radicals containing 1 to 20 carbon atoms, cycloalkyl radicals containing 5 to 20 carbon atoms, aralkyl radicals containing 7 to 12 carbon atoms, and aryl radicals containing 6 to 12 carbon atoms; or a mixture thereof.

11. The process according to claim 10 wherein $R^9$ and $R^{10}$ are independently selected from methyl, ethyl, propyl, butyl, pentyl, isopentyl, hexyl, and heptyl and $R^{11}$ is independently selected from hydrogen, methyl, ethyl, propyl, pentyl, and hexyl.

12. The process according to any one of claims 7, 8, or 9 wherein said hydroformylation solvent comprises N-methyl-2-pyrrolidinone; at least one N,N-disubstituted amide selected from N,N-dimethylformamide,, N,N-diethylformamide, N,N-diethylacetamide, N,N-diethyldodecanamide, N,N-dibutyldodecanamide, N-methyl-N-butyldodecanamide, N,N-diethyltetradecanamide, N,N-dicyclohexyldecanamide, N,N-dibutylbenzamide, and N,N-dibenzyloctanamide; or a mixture thereof.

13. The process according to any one of claims 7, 8, or 9 wherein said hydroformylation solvent comprises N,N-dimethylacetamide.

14. A process for the preparation of glycolaldehyde consisting essentially of contacting formaldehyde, hydrogen and carbon monoxide with a catalyst solution, consisting essentially of:
(i) at least one fluorophosphite compound having the general formula (I):

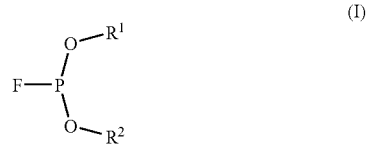

wherein $R^1$ and $R^2$ collectively represent alkylene of 2 to 12 carbon atoms, cyclohexylene, an arylene group having the formula

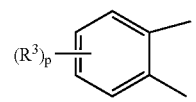

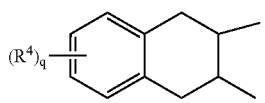

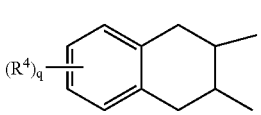

or a radical having the formula

wherein
- each of $A^1$ and $A^2$ is an arylene radical having formula (V), (VI) or (VII) above wherein each ester oxygen atom of fluorophosphite (I) is bonded to a ring carbon atom of $A^1$ and $A^2$;
- X is (i) a chemical bond directly between ring carbon atoms of $A^1$ and $A^2$; or (ii) an oxygen atom, a group having the formula —$(CH_2)_y$— wherein y is 2 to 4, or a group having the formula

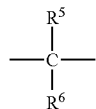

wherein
- $R^5$ is hydrogen, alkyl or aryl; $R^6$ is hydrogen or alkyl;
- and the group —$C(R^5)(R^6)$— contains up to 8 carbon atoms; and wherein
- $R^3$ and $R^4$ are independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of such alkyl, alkoxy, alkanoyl, alkoxycarbonyl and alkanoyloxy groups contains up to about 8 carbon atoms; and p and q each is 0, 1 or 2;

(ii) rhodium; and (iii) a hydroformylation solvent consistently essentially of at least one N,N-disubstituted amide, N-substituted cyclic amide, or a mixture thereof.

15. The process according to claim 14 wherein said fluorophosphite compound has formula (VIII):

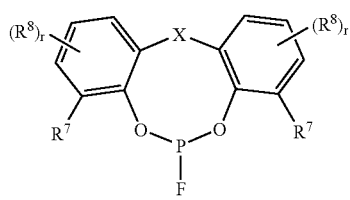

(VIII)

wherein $R^7$ represents halogen or $C_3$ to $C_8$ alkyl; $R^8$ represents hydrogen, halogen, $C_1$ to $C_8$ alkyl, or $C_1$ to $C_8$ alkoxy; r is 0, 1 or 2; and X is a group having the formula

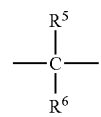

wherein $R^5$ and $R^6$ each are hydrogen or alkyl.

16. The process according to claim 15 wherein said fluorophosphite compound has formula (IX):

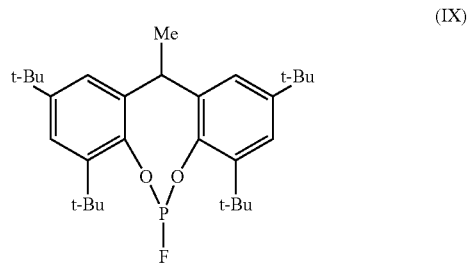

(IX)

wherein t-Bu is tertiary butyl and Me is methyl.

17. The process according to claim 14 wherein said hydroformylation solvent consists essentially of N-methyl-2-pyrrolidinone; at least one N,N-disubstituted amide selected from N,N-dimethylformamide, N,N-diethylformamide, N,N-diethylacetamide, N,N-diethyldodecanamide, N,N-dibutyldodecanamide, N-methyl-N-butyldodecanamide, N,N-diethyltetradecanamide, N,N-dicyclohexyldecanamide, N,N-dibutylbenzamide, and N,N-dibenzyloctanamide; or a mixture thereof.

* * * * *

UNITED STATES PATENT AND TRADEMARK OFFICE
CERTIFICATE OF CORRECTION

PATENT NO.       : 7,301,054 B1                                    Page 1 of 1
APPLICATION NO.  : 11/693542
DATED            : November 27, 2007
INVENTOR(S)      : Puckette It is certified that error appears in the above-identified patent and that said Letters Patent is hereby corrected as shown below:

Column 22, lines 50-58, read:

"
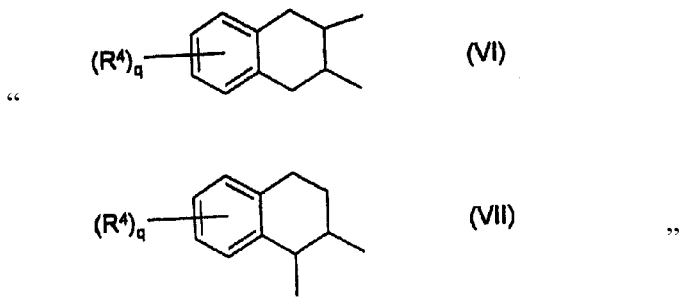

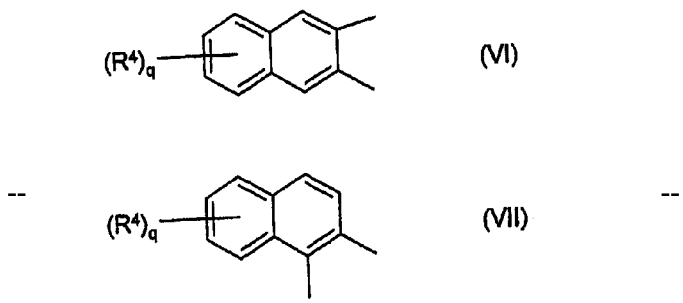
"

but should read:

--
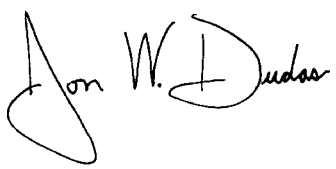
--

Signed and Sealed this

Twenty-ninth Day of July, 2008

JON W. DUDAS
*Director of the United States Patent and Trademark Office*